United States Patent [19]
Towsley

[11] Patent Number: 6,036,665
[45] Date of Patent: Mar. 14, 2000

[54] ORTHOPEDIC FOOT, ANKLE AND LOWER LEG BRACE

[76] Inventor: Harold E. Towsley, 1821 Greenstone Dr., New Haven, Ind. 46774

[21] Appl. No.: 09/039,517

[22] Filed: Mar. 16, 1998

[51] Int. Cl.[7] .................................................. A61F 5/00
[52] U.S. Cl. ............................... 602/23; 602/16; 602/27; 602/29
[58] Field of Search ......................... 602/16, 20, 23–26, 602/29; 128/882

[56] References Cited

U.S. PATENT DOCUMENTS

| | | | |
|---|---|---|---|
| 1,340,630 | 5/1920 | Maddox | 602/20 |
| 3,230,952 | 1/1966 | Terron | 602/23 |
| 5,267,949 | 12/1993 | De La Torre et al. | 602/23 X |
| 5,662,594 | 9/1997 | Rosenblatt | 602/16 |
| 5,669,873 | 9/1997 | Towsley | 602/26 |

*Primary Examiner*—Richard J. Apley
*Assistant Examiner*—Jayne Saydah
*Attorney, Agent, or Firm*—Taylor & Associates, P.C.

[57] ABSTRACT

Apparatus and techniques for arresting or correcting lower leg, ankle and foot deformities which readily adapt themselves to progressive application of corrective forces to the deformed body portion. A brace is composed of a plurality of articulated portions with fasteners joining the articulated portions. Certain fasteners are periodically released, brace portions relatively moved to new locations and the fasteners relocked to apply renewed corrective bending moments or torques to portions of the anatomy.

12 Claims, 3 Drawing Sheets

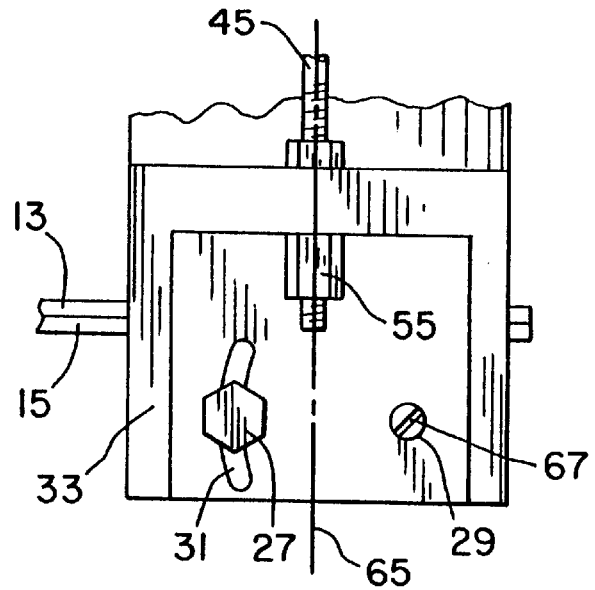
FIG_5
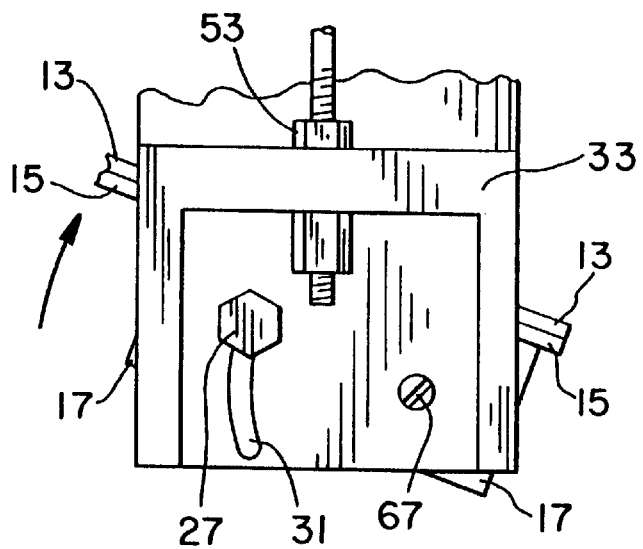
FIG_7

ORTHOPEDIC FOOT, ANKLE AND LOWER LEG BRACE

SUMMARY OF THE INVENTION

The present invention relates generally to orthopedic appliances of the type employed to arrest or correct deformation of a body part or to otherwise support, supplement or immobilize weakened joints and more particularly to such devices for arresting or correcting anatomical deformities associated with the foot or lower portion of a human leg. In particular, the present invention seeks to correct deformities in young patients such as club foot, bowed or other tibia or fibula problems, and pigeon-toed or similar foot or ankle alignment problems.

Correction of many abnormalities such as the club foot problem is more easily accomplished when the patient is young, preferably in infancy. It is also recognized that the congenital club foot problem be initially treated non-operatively, for example, by daily manipulation of the foot followed by adhesive tape strapping or the application of a corrective plaster cast. Such techniques do not readily adapt themselves to progressive application of corrective forces to the deformed foot.

There have been numerous attempts over the years to create external appliances using brackets, clamps, bindings and other mechanisms to correct leg and foot abnormalities. For example, in U.S. Pat. No. 3,086,522 there is shown a platform to which a shoe-like foot receptacle is affixed and including an upstanding pipe reward of the shoe supporting a series of leg clamps. The shoe portion includes two portions which are pivotable about vertical axes. Additionally, the pipe may be positioned in any of a variety of positions relative to the platform or base by use of a ball and socket joint between the two. In addition to being cumbersome, any force or bending of the foot relative to the leg must take place along an axis which passes through this ball and socket joint. Also, this patented device requires the user to remain in a position with the knee bent at nearly ninety degrees.

A similar patented device requiring the user to remain in a position with the knee bent at nearly ninety degrees is shown in U.S. Pat. No. 3,304,937. The only forces which may be applied to the wearer's foot with this device are twisting moments about a vertical axis generally aligned with the wearer's lower leg.

An early attempt at treating the club foot problem is shown in U.S. Pat. No. 9,472 and included bindings for gripping both lower legs in a relatively fixed location and a pair of foot platforms pivotable about longitudinal and transverse axes beneath the platform as well as allowing a toe-in, toe-out correction to be applied. While the knee need not remain bent with this device, both legs are fixed together so that both knees must flex in unison if at all.

Finally, waist, thigh and lower leg bindings attached to a foot platform in U.S. Pat. No. 265,942 allow a rack and pinion arrangement to apply forces tending to twist the foot so that the sole faces inwardly or outwardly.

What these patents have in common is a lack of any capacity to apply multiple medial and lateral bending moments at preferred locations along the leg, an inability to apply both toe-up/toe-down and toe-in/toe-out bending moments about mutually perpendicular axes which pass through or close to the joint region under treatment, an undesirably severe restriction in mobility, and a continued recognition of a need for a versatile, compact, and easily applied foot and ankle brace for arresting or correcting such deformities.

Among the several objects of the present invention may be noted the provision of an entirely exterior foot and lower leg brace; the provision of a highly individualizable orthopedic brace for arresting or correcting club foot, pigeon-toed, bow legged or other foot or ankle abnormalities; the provision of an orthopedic brace in accordance with the previous object especially suited for treating infants or young children; the provision of an externally applied (non-invasive) foot and ankle appliance which may be easily and repeatedly modified to urge certain portions of the foot or lower leg in selected directions and by selected amounts relative to other portions of the foot or lower leg; and the provision of a unique foot and ankle brace. These as well as other objects and advantageous features of the present invention will be in part apparent and in part pointed out hereinafter.

In general, an orthopedic appliance or brace has at least first, second third and fourth articulated segments or portions with the first and second segments pivotably joined as a pair for relative angular movement about a first axis. The second and third segments are pivotably joined as a pair for relative angular movement about a second axis which extends generally perpendicular to the first axis. The third and fourth segments are similarly pivotably joined as a pair for angular movement about yet a third axis which extends generally perpendicular to the first and second axes. There is one or more threaded fasteners associated with each pair of segments for selectively restricting relative pivotal movement between the pair. Each pair may be fixed at selected relative angular orientations by these fasteners.

BRIEF DESCRIPTION OF THE DRAWING

FIG. 5 is a side elevation view of a portion of the device as viewed from the left of FIG. 4;

FIG. 7 is a side elevation view similar to FIG. 5, but illustrating the fourth segment of the device adjusted to a toe-up position.

Corresponding reference characters indicate corresponding parts throughout the several views of the drawing.

The exemplifications set out herein illustrate a preferred embodiment of the invention in one form thereof and such exemplifications are not to be construed as limiting the scope of the disclosure or the scope of the invention in any manner.

DESCRIPTION OF THE PREFERRED EMBODIMENT

Figure 1:
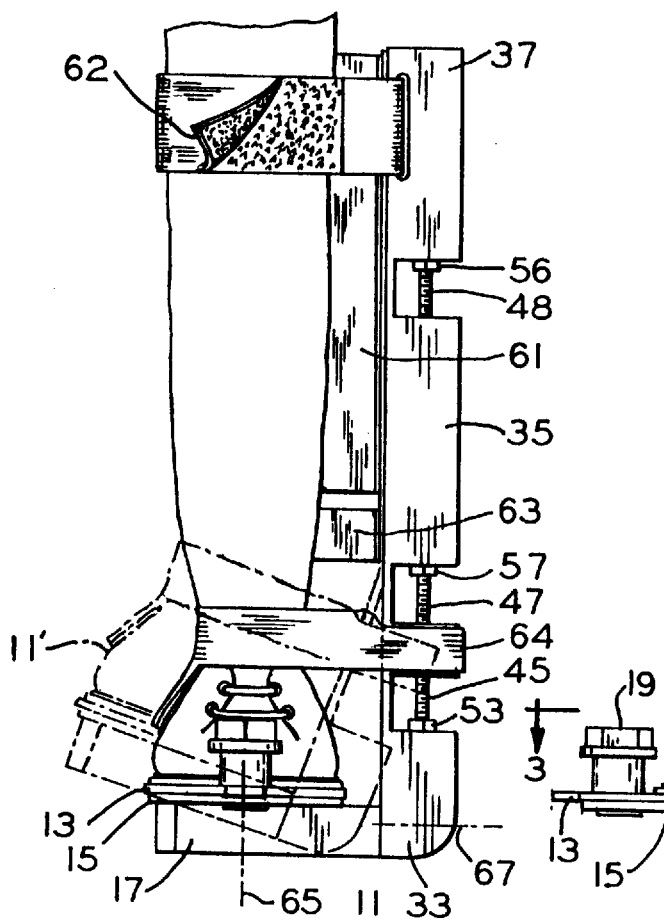
FIG. 1 is a front elevation view of an orthopedic device according to the present invention applied to the lower leg and foot of a patient.
Figure 2:
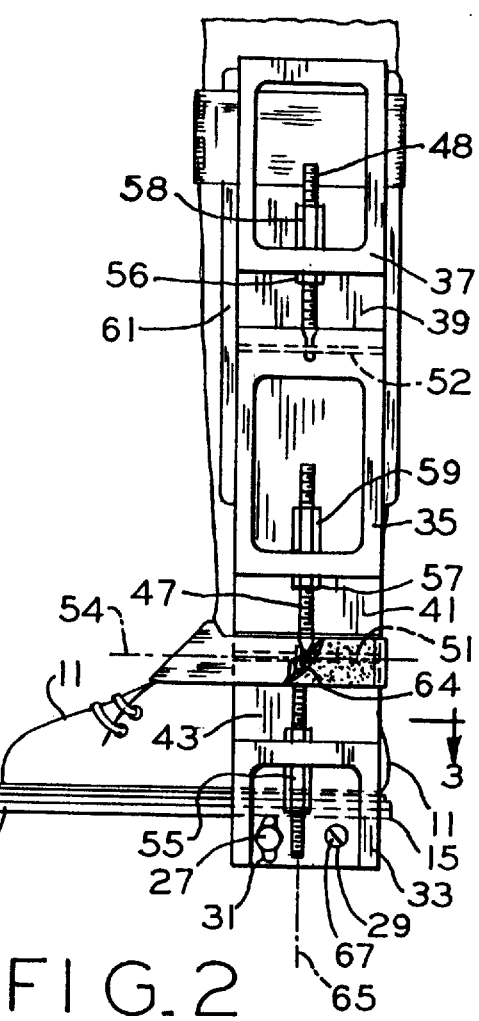
FIG. 2 is a side elevation view of the device of FIG. 1.
Figure 3:
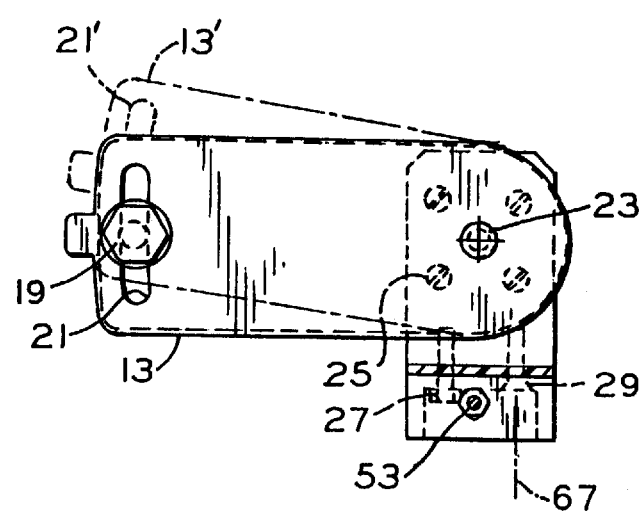
FIG. 3 is a view in cross-section along lines 3—3 of FIG. 2.

In FIGS. 1–3, a child's shoe 11 is fastened to a relatively flat platform or plate 13 by hook-and-loop fastening materials such as VELCRO with one sheet glued to the bottom of the shoe 11 and a mating sheet glued to the top of a foot platform 13, by permanent adhesive attachment, or by any other suitable technique. Platform 13 is supported by an adjacent relatively flat platform or plate 15. Platforms 13 and 15 are joined by a screw 23 located beneath the heel of the shoe 11, passing through both platforms and into a block or base 17 as well as by a locking screw, thumb nut or similar fastener 19 which passes through the arcuate opening 21. Fastener 19 may be fixed relative to platform 15, or the platform 15 may have an arcuate slot similar to 21 with fastener 19 movable in each slot thereby nearly doubling the arcuate adjustment range. The lower or base platform 15 is additionally affixed to the block 17 by several additional screws such as 25 which do not pass through platform 13. Thus, platform 13 is free to pivot about screw 23 so long as the locking screw 19 is loose, but tightening that locking screw fixes the relative angular relationship between the foot and base platforms, and therefor, the angular relationship of the shoe 11 about a vertical axis 65 with respect to the remainder of the brace.

Block 17 is fastened to the upstanding leg portion of the brace by screws 27 and 29. Screw 29 provides an articulated joint between the two segments while screw 27 functions to selectively clamp the two segments at preferred angular orientations performing much the same as screws 23 and 19. The upstanding leg portion of the brace is formed from a plurality of generally longitudinally aligned rigid members such as 33, 35 and 37 which are pivotably coupled together by interconnecting webs such as 39, 41 and 43 for relative angular movement about a bending moment axis such as 54 which is generally parallel to and fairly close to the corresponding transverse pins such as 51. The axes such as 54 are mobile, not fixed, and are located sometimes to one side and at other times to the other side of the brace. The angular movement of the pivotably coupled pair 35 and 37 about the bending moment axis is selectively restricted by the threaded rod or eye-bolt 48 which has an eye 50 for engaging the transverse pin 52 in the adjacent member 35. Thus, for example, tightening of the nut 58 against member 37 functions to pull the adjacent rigid members 35 and 37 angularly toward one another, while loosening nut 58 and tightening nut 56 against member 37 tends to rotate members 35 and 37 in an opposite sense. A number of straps, including VELCRO portions or a similar fastening arrangement such as 62 and 64, are included for encircling regions of the patient's leg to secure the rigid members to the leg and to transfer bending moment forces to the patient's leg, foot and/or ankle. Webs 39, 41 and 43 thus allow a variety of bending moments to be applied to the lower leg portion about a plurality of longitudinal axes generally parallel to one another.

Except for being somewhat smaller, the two upper members 35 and 37 and their associated hardware are much the same as the two upper members of the knee brace shown in my U.S. Pat. No. 5,669,873. My continuation-in-part application Ser. No. 08/912,728 utilizes similarly articulated segments to form a spinal column brace. While of a somewhat different shape, the pads 61 and 63 may be attached to the members by VELCRO as in that prior device. Pad 63 is also preferably of a more resilient material. Strap 62 for example, may pass through a pair of slots in the member 37. As in that prior patented device, the pin 52 supports the eye 50 a single threaded rod 48, however, a nut 56 has been added so that web 39 may be flexed in either of two directions from its unstrained position. Loosening nut 58 and tightening nut 56 flexes web 39 one way while loosening nut 56 and tightening nut 58 flexes web 39 the opposite way. Webs 41 and 43 may similarly be flexed in either of two senses. This allows either lateral or medial bending moments to be selectively applied to the lower leg.

While each pin in my prior device supported a single threaded rod, the pin 51 passes through both eyes of threaded rods 45 and 47 and those rods or eye-bolts extend in opposite directions therefrom. Web portions 41 and 43 may be thought of as forming a single web pivotably joining segments 33 and 35 with a thickened intermediate region 42 for supporting the pivot pin 51. This allows webs 41 and 43 to be located much closer to one another than was heretofor possible. In turn, a more precise corrective bending moment using a combination of flexing of those webs may be applied in the region of the ankle. Moreover, the brace is capable of providing independent torque or bending moment corrective forces about any of three mutually perpendicular axes, a vertical axis 65 coaxial with screw 23 and extending generally along the lower leg bones, selected ones of several generally parallel longitudinal axes which run parallel to the pins 51 and 52, and a transverse axis 67 which extends coaxially with screw 29.

Figure 4:
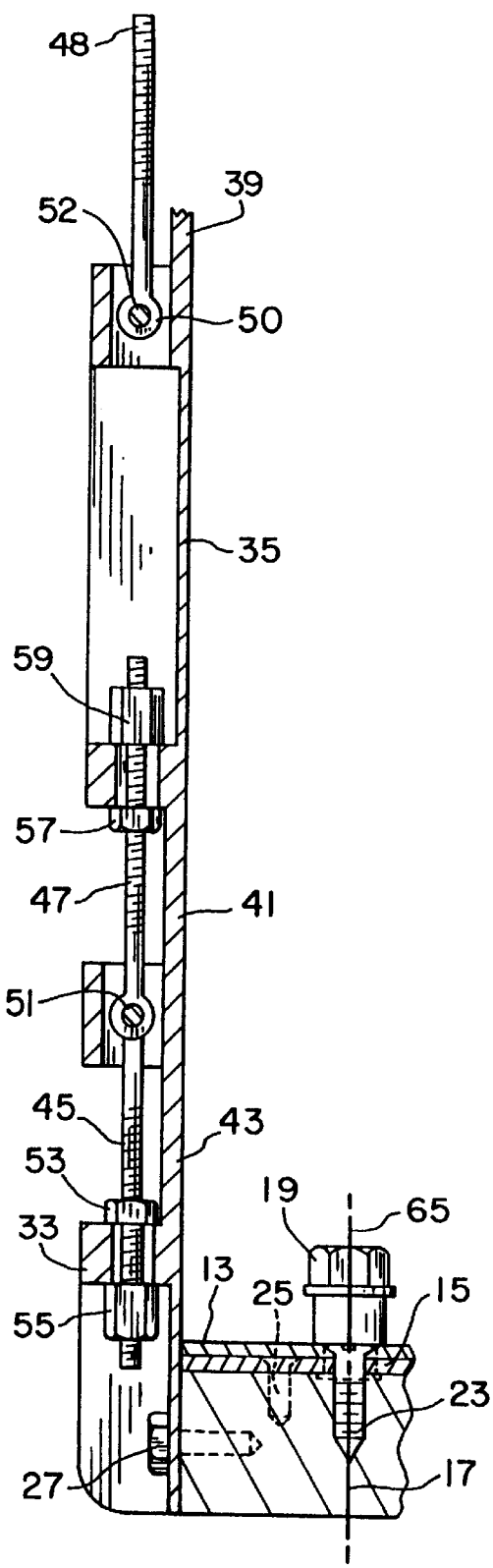
FIG. 4 is a partial rear view in cross-section from the right side of FIG. 2 with the padding, and patient's leg and shoe omitted.
Figure 6:
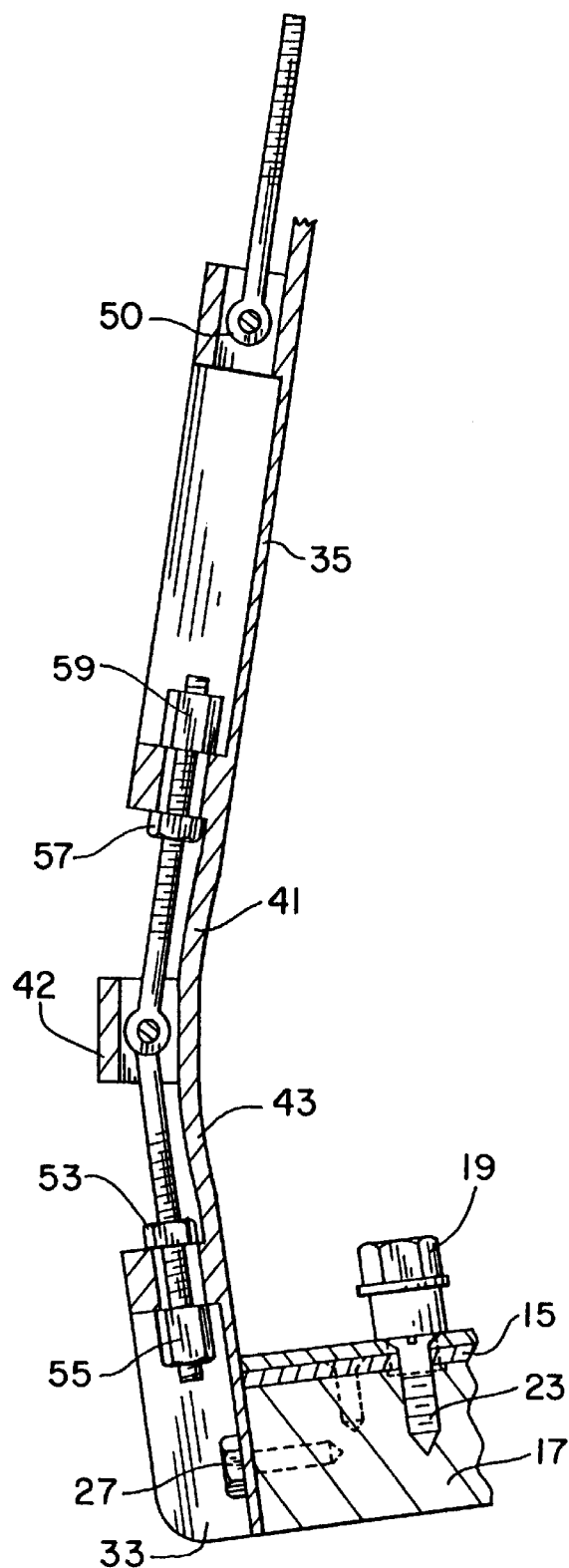
FIG. 6 is a rear cross-sectional view similar to FIG. 4. but illustrating adjustment of the device to apply a bending moment to correct an inverted club foot deformity where the sole faces inwardly.

The method of application and use of the invention should now be clear. FIG. 1 shows a front view of an infant's left leg with the brace applied to the outer or lateral portion of the leg to correct an inverted club foot (sole facing inward). By progressively loosening the nut 59 and tightening the nut 57, the brace is flexed about web 41 and the shoe 11' is urged counterclockwise about a longitudinal axis at or slightly above ankle level as viewed, from the dotted line position toward the solid line position. A similar bending moment could be applied at or slightly below the ankle flexing the brace about web 43 by loosening nut 55 and tightening nut 53. This is illustrated by the transition from FIG. 4 to FIG. 6. Thus, FIGS. 1 and 6 illustrate application of a lateral bending moment between the infant's leg and foot. Application of a medial bending moment may also be achieved by flexing the brace, for example, about web 43 in an opposite sense by loosening nut 53 and tightening nut 55. Initially, in FIGS. 1 and 6, this would result in the segments moving angularly away from one another. This may be employed to correct for the less common everted club foot (sole facing outwardly). By selective adjustment of the nuts 56, 58, 57 and 59, bending moments for correcting either bowed-in or bowed-out conditions of the lower leg are also possible.

The technique for correcting a pigeon-toed or toe-in condition is best seen in FIG. 3. The foot platform 13 is illustrated as initially occupying a pigeon-toed (toe in) position 13'. Here, the shaft of screw 19 is near the top of the arcuate slot 21. By loosening nut 19, the upper or foot platform may be pivoted counterclockwise as viewed about the screw 23, that is, about a vertical axis which extends generally along the lower leg and then re-locked locating the foot in a new more nearly anatomically correct position. Periodically, the nut 19 is again released and a new torque about the axis of screw 23 is applied to further urge the foot toward its normal position. Clearly, a somewhat reversed process is used to correct a toe-out condition.

The correction of toe-up and toe-down abnormalities is best seen in FIGS. 5 and 7 where a toe-up condition is initially illustrated by the foot platform 13 and base platform 15 both being elevated or rotated in a clockwise direction as viewed about the transverse axis of screw 29. To apply a corrective toe-down torque to the patient's foot, screw 27 is loosened and the toe end of the platforms depressed toward the position illustrated in FIGS. 2 and 5. With such depression, the shaft of screw 27 moves along the arc of slot 31. When sufficient corrective torque has been applied, the screw 27 is again tightened. As with all the other corrective measures, this process is typically repeated over a period of time until the foot assumes a normal position without urging.

Similarly, correction of a toe-down condition begins with the screw 27 shaft near the bottom of the arcuate slot 31.

In summary, the orthopedic appliance has at least a first 35, second 33, third 15, 17 and fourth 13 articulated segments. The first and second segments 35 and 33 are pivotably joined as a pair for relative angular movement about a longitudinal first axis 54. Axis 54 is migratory in the sense that its location is on the side of the brace having the smaller included angle between the brace segments, e.g., toward the right in FIG. 6 and toward the left in FIG. 1. Also, the location of axis 54 is higher or lower depending on the amount by which the nuts on each of the threaded fastener 47 or 45 is adjusted. The second segment 33 and third segment 15, 17 are pivotably joined as a pair for relative angular movement about a second transverse axis 67 which extends generally orthogonal to the first or longitudinal axis 54. The third segment 15, 17 and the fourth segment 13 are pivotably joined as a pair for angular movement about a third vertical axis 65 which extends generally orthogonal to the first and second axes. Each pair of segments has an arrangement for selectively restricting relative pivotal movement between the two pair segments. For example, the pair 35 and 33 are anchored by the locations of the nuts 53, 55, 57 and 59. The pair 33 and 15, 17 are anchored by tightening the screw 27. Similarly, pair 13 and 15, 17 are locked at a preferred angular position by the clamping nut 19.

From the foregoing, it is now apparent that a novel foot, ankle and lower leg orthopedic device for correcting a variety of deformities has been disclosed meeting the objects and advantageous features set out hereinbefore as well as others, and that numerous modifications as to the precise shapes, configurations and details may be. For example, while hexagonal nuts have been illustrated, knurled knobs or other threaded fasteners may be preferred for some applications. Buckles or other quick release fasteners may be substituted for the VELCRO straps. Simple alignment pins may be used instead of the screws such as 25 or 29. The shoe 11 may be replaced by foot securing straps. These as well as other modifications made by those having ordinary skill in the art without departing from the spirit of the invention or the scope thereof as set out by the claims which follow.

What is claimed is:

1. An orthopedic brace including at least two hollowed-out parallelepiped portions joined along a relatively thin web of flexible material common to the two portions to provide relative pivotal motion between the two portions, means for selectively restricting relative pivotal movement between the two portions including a pair of elongated threaded rods pivotably joined together adjacent the relatively thin web and extending in generally opposite directions through respective ends of the parallelepiped portions and into the hollowed-out regions thereof, and a pair of nuts threadedly engaging the rods and helically movable therealong to selectively pull the parallelepiped portions angularly toward one another.

2. The orthopedic brace of claim 1 further comprising a third hollowed-out parallelepiped portion joined to one said hollowed-out parallelepiped portion to form a pair by a further relatively thin web, the third hollowed-out parallelepiped portion and said one hollowed-out parallelepiped portion having a third threaded rod and third nut extending therebetween for selectively restricting pivotal movement between the portions of the pair.

3. The orthopedic brace of claim 2 wherein the third threaded rod extends into the hollowed out portion and further comprising an additional nut threadedly engaging the third rod within the third parallelepiped portion hollowed-out region and helically movable therealong, and cooperating with the third nut to selectively pull the third parallelepiped portion and said one hollowed-out parallelepiped portion angularly toward and away from one another.

4. The orthopedic brace of claim 1 wherein the pair of elongated threaded rods each comprise eye-bolts and are pivotably joined together by a hinge pin passing through both eye ends of the eye-bolts.

5. The orthopedic brace of claim 4 wherein the relatively thin web includes a thickened region intermediate the two portions with a pair of thin web portions extending in opposite directions therefrom and the hinge pin passes transversely through the thickened region.

6. An orthopedic brace including at least two hollowed-out parallelepiped portions joined along a relatively thin web of flexible material common to the two portions to provide relative pivotal motion between the two portions, means for selectively restricting relative pivotal movement between the two portions including an elongated threaded rod pivotably joined to one parallelepiped portion and extending therefrom along the web and through an end of the other parallelepiped portion into the hollowed-out region thereof, and a pair of nuts threadedly engaging the rod, one nut on either side of the other parallelepiped end, and helically movable therealong to selectively pull the parallelepiped portions angularly toward and away from one another.

7. An orthopedic appliance for application to a human being from the lower leg to the foot and spanning the ankle region, said orthopedic appliance having at least first, second, third and fourth articulated segments, the first and second segments pivotably joined as a pair for relative angular movement about a first axis, said first axis extending longitudinally with pivotal motion thereabout selectively applying medial and lateral bending moments between the lower leg and foot, the second and third segments pivotably joined as a pair for relative angular movement about a second axis generally orthogonal to said first axis, and the third and fourth segments pivotably joined as a pair for angular movement about a third axis generally orthogonal to the first and second axes, each pair of segments having means for selectively restricting relative pivotal movement between the two pair segments.

8. An orthopedic appliance for application to a human being from the lower leg to the foot and spanning the ankle region, said orthopedic appliance having at least first, second, third and fourth articulated segments, the first and second segments pivotably joined as a pair for relative angular movement about a first axis, the second and third segments pivotably joined as a pair for relative angular movement about a second axis generally orthogonal to said first axis, said second axis extending transversely with pivotal motion thereabout selectively applying toe-up and toe-down bending moments between the lower leg and foot, and the third and fourth segments pivotably joined as a pair for angular movement about a third axis generally orthogonal to the first and second axes, each pair of segments having means for selectively restricting relative pivotal movement between the two pair segments.

9. An orthopedic appliance for application to a human being from the lower leg to the foot and spanning the ankle region, said orthopedic appliance having at least first, second, third and fourth articulated segments, the first and second segments pivotably joined as a pair for relative angular movement about a first axis, the second and third segments pivotably joined as a pair for relative angular movement about a second axis generally orthogonal to said first axis, and the third and fourth segments pivotably joined as a pair for angular movement about a third axis generally orthogonal to the first and second axes, said third axis extending vertically generally along the lower leg with pivotal motion thereabout selectively applying toe-in and toe-out bending moments between the lower leg and foot, each pair of segments having means for selectively restricting relative pivotal movement between the two pair segments.

10. An orthopedic appliance having at least first, second, third and fourth articulated segments, the first and second segments pivotably joined as a pair for relative angular movement about a first axis, the second and third segments pivotably joined as a pair for relative angular movement about a second axis generally orthogonal to said first axis, and the third and fourth segments pivotably joined as a pair for angular movement about a third axis generally orthogonal to the first and second axes, at least one of the third and fourth segments having an arcuate slot therein, the third and fourth segments comprising a pair of superposed relatively flat platforms pivotably joined and configured to be positioned beneath the heel of the foot, each pair of segments having means for selectively restricting relative pivotal movement between the two pair segments, said means for selectively restricting relative pivotal movement comprising a clamping nut extending through one platform and passing through the arcuate slot of the other platform.

11. The orthopedic appliance of claim 10 wherein both the third and the fourth segment have arcuate slots, the fourth segment further including on the upper surface thereof one sheet of hook-and-loop fastening material for receiving a shoe with a mating sheet of hook-and-loop fastening material on the sole thereof.

12. The orthopedic appliance of claim 11 wherein the third segment includes a base portion beneath the heel of the foot and on the side thereof opposite the fourth segment and the third and fourth segments are pivotably joined by a screw passing through the fourth portion and into the base portion, and further comprising a second screw pivotably joining the second and third segments passing through the second segment and into the base, and the means for selectively restricting relative pivotal movement between the second and third segments comprises an arcuate slot in the second segment and a third screw passing through the arcuate slot and into the base.

* * * * *